(12) United States Patent
Miller et al.

(10) Patent No.: US 9,779,631 B1
(45) Date of Patent: Oct. 3, 2017

(54) FACILITATING PATIENT COMMUNICATION USING BRANCHING LOGIC IN AN OUTPATIENT ONCOLOGY TREATMENT REGIMEN

(71) Applicant: WALGREEN CO., Deerfield, IL (US)

(72) Inventors: Richard Miller, Bethel Park, PA (US); Amy Pfeifer, Chicago, IL (US); Rhonda Letwin, Pittsburg, PA (US)

(73) Assignee: WALGREEN CO., Deerfield, IL (US)

( * ) Notice: Subject to any disclaimer, the term of this patent is extended or adjusted under 35 U.S.C. 154(b) by 326 days.

(21) Appl. No.: 13/779,395

(22) Filed: Feb. 27, 2013

(51) Int. Cl.
*G09B 23/28* (2006.01)
*G09B 5/00* (2006.01)

(52) U.S. Cl.
CPC ...................................... *G09B 5/00* (2013.01)

(58) Field of Classification Search
USPC ......................................................... 434/362
See application file for complete search history.

(56) References Cited

U.S. PATENT DOCUMENTS

| | | | | |
|---|---|---|---|---|
| 5,633,910 A | * | 5/1997 | Cohen .............................. | 379/38 |
| 2004/0034286 A1 | * | 2/2004 | Kasper ................. | A61B 5/0002 600/300 |
| 2005/0102159 A1 | * | 5/2005 | Mondshine ........................ | 705/2 |
| 2008/0097784 A1 | * | 4/2008 | Miller et al. ....................... | 705/2 |
| 2009/0043608 A1 | * | 2/2009 | Nadas et al. ....................... | 705/3 |
| 2009/0205042 A1 | * | 8/2009 | Zhou et al. ....................... | 726/19 |
| 2009/0259495 A1 | * | 10/2009 | Rosenfeld .......................... | 705/3 |
| 2011/0087501 A1 | * | 4/2011 | Severin ............................. | 705/3 |
| 2011/0229867 A1 | * | 9/2011 | Gough ..................... | G09B 7/02 434/323 |
| 2012/0173269 A1 | * | 7/2012 | Omidi .................... | G06Q 50/22 705/2 |

* cited by examiner

*Primary Examiner* — Thomas Hong
(74) *Attorney, Agent, or Firm* — Marshall, Gerstein & Borun LLP; Randall G. Rueth

(57) ABSTRACT

A method and system facilitate communication with a patient on an outpatient oral oncology regimen. The method and system facilitate creating an initial contact guide to direct a patient interaction occurring at the beginning of the outpatient oral oncology regimen and using the initial contact guide to conduct an initial contact with the patient using the branching logic of the initial contact guide to determine which initial contact guide questions and informational scripts to present based on information provided by the patient. The method and system further facilitate creating a secondary contact guide to conduct a secondary, follow-up contact with the patient using the branching logic of the secondary contact guide to determine which secondary contact guide questions and informational scripts to present based on information provided by the patient.

21 Claims, 5 Drawing Sheets

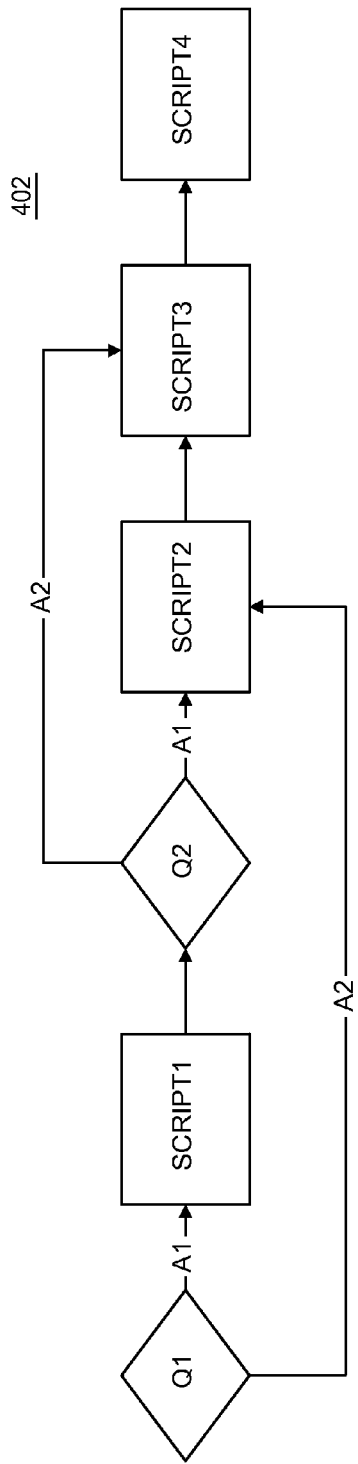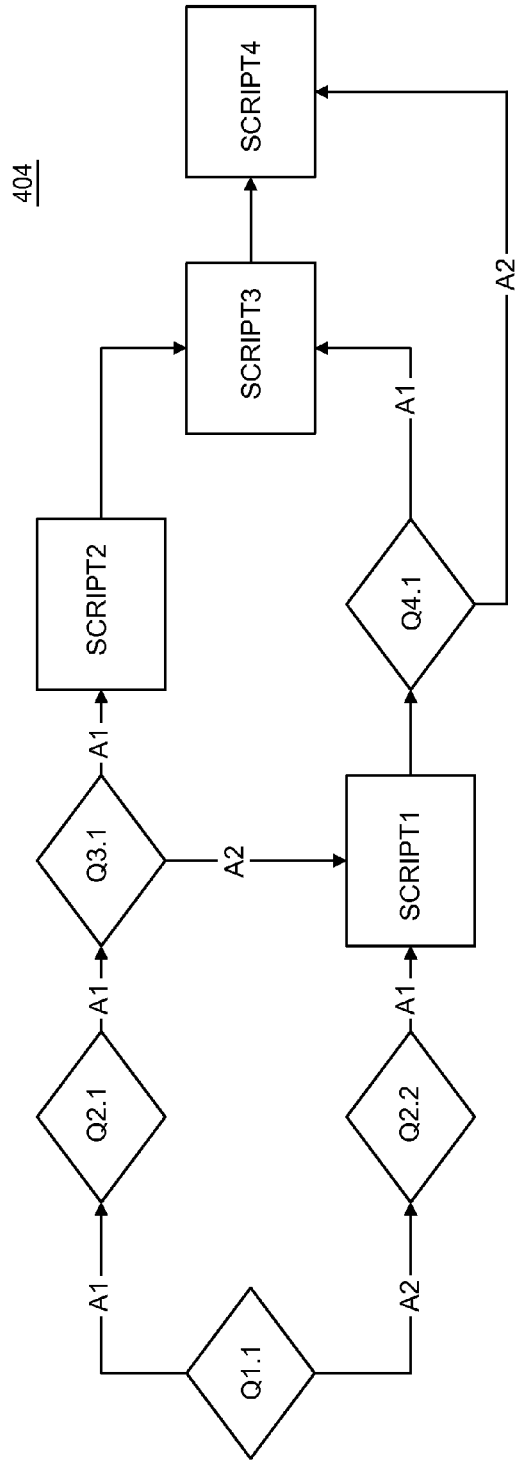
FIG. 4A
FIG. 4B

FACILITATING PATIENT COMMUNICATION USING BRANCHING LOGIC IN AN OUTPATIENT ONCOLOGY TREATMENT REGIMEN

FIELD OF INVENTION

The present disclosure generally relates to a system and method for guiding interactions between a technician or clinician and a patient and, more particularly to an interaction guiding system and method to assist a pharmacist in monitoring patient treatment compliance, monitoring side effects, and educating patients taking outpatient oral oncology medication.

BACKGROUND

Since the 1940s, cancer patients have been treated with chemotherapy medications to shrink tumors. Traditionally, these chemotherapy and other cancer treatment medications have been administered under the direct supervision of a medical professional in an out-patient clinic or an in-patient hospital. Patients well enough to not be hospitalized would have to travel to their doctor's clinic to receive their treatment. If a patient lives in a rural area or far away from his or her doctor's office, a trip to his or her doctor's office may be a long ordeal. More recently, medical science has created oral oncology medication that patients can take anywhere. While these treatments may be taken at home like other medications, they are still powerful drugs designed to treat cancer according to regular treatment plans that must be assiduously followed. However, because patients may be self-administering the medication, there likely is no direct medical supervision of whether the patient is taking the medication as prescribed or what side effects the patient may be experiencing. Thus, it is very important for healthcare providers to be able to have a capability of asking patients whether they are following the treatment plan or having side effects as well as provide medication counseling and education about the medication between doctor's appointments.

SUMMARY OF THE DISCLOSURE

Accordingly, it may be advantageous to create a system which can drive communication with patients to gather information during the course of treatment. Further, to contain costs, it may be advantageous to use a computer system to generate a set of questions and informational scripts to present to patients with branching logic to adapt the set of questions and informational scripts in real time.

In an embodiment, a method for communicating with a patient on an outpatient oral oncology regimen, including: creating an initial contact guide to direct a patient interaction occurring at the beginning of the outpatient oral oncology regimen, wherein the initial contact guide includes one or more questions, one or more informational scripts, and branching logic to determine which questions and informational scripts to present and an order in which questions and informational scripts are presented; using the initial contact guide to conduct an initial contact with the patient by: (i) presenting a first initial contact question to the patient, (ii) receiving an initial contact answer from the patient wherein the initial contact answer is stored in a patient interaction database, (iii) using the branching logic of the initial contact guide to determine which initial contact guide questions and informational scripts to present based on the initial contact answer, and (iv) presenting one or more subsequent questions or informational scripts based on the determination of which initial contact guide questions and informational scripts to present based on the initial contact answer; creating a secondary contact guide to direct a patient interaction occurring a first period of time after the beginning of the outpatient oral oncology regimen, wherein the secondary contact guide includes one or more questions, one or more informational scripts, and branching logic to determine which questions and informational scripts to present and an order in which questions and informational scripts are presented; and using the secondary contact guide to conduct a secondary contact with the patient by: (i) after the first period of time after the beginning of the outpatient oral oncology regimen, presenting a first secondary contact question to the patient, (ii) receiving a secondary contact answer from the patient wherein the secondary contact answer is stored in a patient interaction database, (iii) using the branching logic of the secondary contact guide to determine which secondary contact guide questions and informational scripts to present based on the secondary contact answer, and (iv) presenting one or more subsequent questions or informational scripts based on the determination of which secondary contact guide questions and informational scripts to present based on the secondary contact answer.

In another embodiment, a computer system including a processor; and a program memory storing executable instructions that when executed by the processor cause the computer system to: create an initial contact guide to direct a patient interaction occurring at the beginning of the outpatient oral oncology regimen, wherein the initial contact guide includes one or more questions, one or more informational scripts, and branching logic to determine which questions and informational scripts to present and an order in which questions and informational scripts are presented; use the initial contact guide to conduct an initial contact with the patient by: (i) present a first initial contact question to the patient, (ii) receive an initial contact answer from the patient wherein the initial contact answer is stored in a patient interaction database, (iii) use the branching logic of the initial contact guide to determine which initial contact guide questions and informational scripts to present based on the initial contact answer, and (iv) present one or more subsequent questions or informational scripts based on the determination of which initial contact guide questions and informational scripts to present based on the initial contact answer; create a secondary contact guide to direct a patient interaction occurring a first period of time after the beginning of the outpatient oral oncology regimen, wherein the secondary contact guide includes one or more questions, one or more informational scripts, and branching logic to determine which questions and informational scripts to present and an order in which questions and informational scripts are presented; and use the secondary contact guide to conduct a secondary contact with the patient by: (i) after the first period of time after the beginning of the outpatient oral oncology regimen, present a first secondary contact question to the patient, (ii) receive a secondary contact answer from the patient wherein the secondary contact answer is stored in a patient interaction database, (iii) use the branching logic of the secondary contact guide to determine which secondary contact guide questions and informational scripts to present based on the secondary contact answer, and (iv) present one or more subsequent questions or informational scripts based on the determination of which secondary contact guide questions and informational scripts to present based on the secondary contact answer.

In another embodiment, a tangible, computer-readable medium storing executable instructions that when executed by a processor of a computer system to: create an initial contact guide to direct a patient interaction occurring at the beginning of the outpatient oral oncology regimen, wherein the initial contact guide includes one or more questions, one or more informational scripts, and branching logic to determine which questions and informational scripts to present and an order in which questions and informational scripts are presented; use the initial contact guide to conduct an initial contact with the patient by: (i) present a first initial contact question to the patient, (ii) receive an initial contact answer from the patient wherein the initial contact answer is stored in a patient interaction database, (iii) use the branching logic of the initial contact guide to determine which initial contact guide questions and informational scripts to present based on the initial contact answer, and (iv) present one or more subsequent questions or informational scripts based on the determination of which initial contact guide questions and informational scripts to present based on the initial contact answer; create a secondary contact guide to direct a patient interaction occurring a first period of time after the beginning of the outpatient oral oncology regimen, wherein the secondary contact guide includes one or more questions, one or more informational scripts, and branching logic to determine which questions and informational scripts to present and an order in which questions and informational scripts are presented; and use the secondary contact guide to conduct a secondary contact with the patient by: (i) after the first period of time after the beginning of the outpatient oral oncology regimen, present a first secondary contact question to the patient, (ii) receive a secondary contact answer from the patient wherein the secondary contact answer is stored in a patient interaction database, (iii) use the branching logic of the secondary contact guide to determine which secondary contact guide questions and informational scripts to present based on the secondary contact answer, and (iv) present one or more subsequent questions or informational scripts based on the determination of which secondary contact guide questions and informational scripts to present based on the secondary contact answer.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIGS. 4A-C depict exemplary embodiments of branching logic that may be used in creating initial, secondary, or tertiary contact guides for use in accordance with the presently described embodiments.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
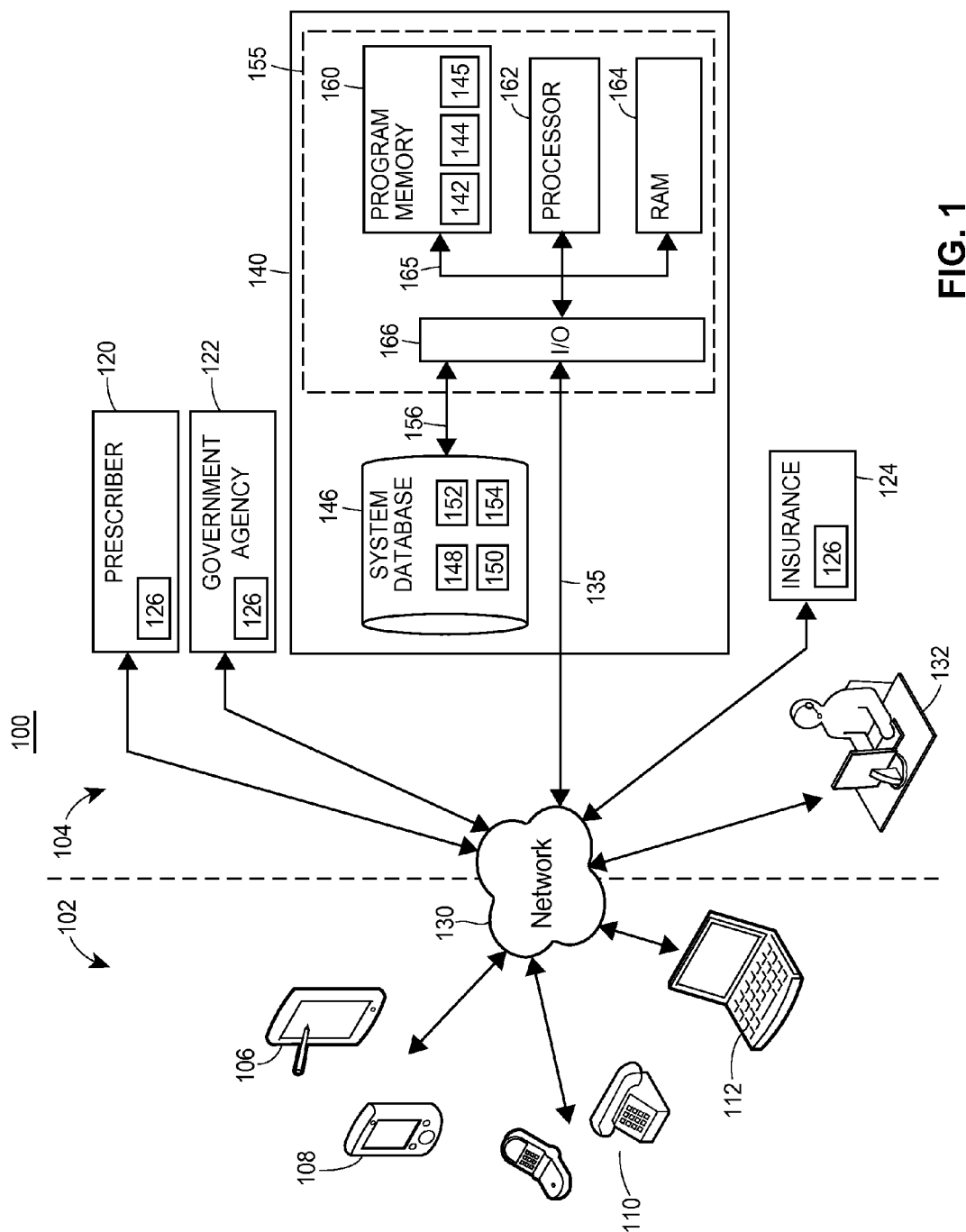
FIG. 1 illustrates a block diagram of a computer network, a computer server, prescriber, government agency, insurance company, representative, and various client devices, on which an exemplary oral oncology medication monitoring system and method may operate in accordance with the described embodiments.

FIG. 1 illustrates a block diagram of an exemplary oral oncology medication monitoring system 100. The high-level architecture includes both hardware and software applications, as well as various data communications channels for communicating data between the various hardware and software components. The oral oncology medication monitoring system 100 may be roughly divided into front-end components 102 and back-end components 104. The front-end components 102 may be one or more different types of client devices with which a patient or caregiver may communicate with the back-end components 104 as discussed herein. The front-end components 102 may include a tablet computer 106, a smart phone 108, a telephone 110 (e.g., a cellular telephone, a landline telephone, a voice over internet protocol telephone, etc.), and/or computer 112 (e.g., laptop computer, desktop computer, terminal, etc.). The various front-end components 102 may be used to communicate with the back-end components 104 in various ways. For example, the front-end components 102 may be used to communicate with the back-end components 104 using voice communication (e.g., using the telephone 110, using an app with voice communication on the tablet 106, etc.), text communication (e.g., SMS messages sent to or from the smartphone 108, a text chat capability of a web browser installed on the computer 112), and/or video communication (e.g., using an audio/video app on the tablet 106). It will be understood that the various front end components include one or more input devices and functions (e.g., microphones, keyboards, touch screens, cameras, computer mice, sensors, etc.) and one or more output devices and functions (e.g., speakers, displays, touch screens, haptic devices, etc.) to facilitate communication between the patient and/or caregiver with the back-end components 104.

The front-end components 102 communicate with the back-end components 104 via the network 130. The network 130 may be a proprietary network, a secure public internet, a virtual private network or some other type of network, such as dedicated access lines, plain ordinary telephone lines, satellite links, combinations of these, etc. Where the network 130 comprises the Internet, data communications may take place over the network 130 via an Internet communication protocol.

The back-end components 104 include a server 140. The server 140 may include one or more computer processors adapted and configured to execute various software applications and components of the oral oncology medication monitoring system 100, in addition to other software applications. The server 140 may have a controller 155 that is operatively connected to the database 146 via a link 156. It should be noted that, while not shown, additional databases may be linked to the controller 155 in a known manner. The controller 155 may include a program memory 160, a processor 162 (may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and program memories 160 may be implemented as semiconductor memories, magnetically readable memories, and/or optically readable memories, for example. The controller 155 may also be operatively connected to the network 130 via a link 135. The server 140 further includes a database 146 or other data storage mechanism (e.g., one or more hard disk drives, optical storage drives, solid state storage devices, etc.). The database 146 is adapted to store data related to the operation of the oral oncology medication monitoring system 100. Such data might include, for example, a medical history database 148, a treatment database 150, a patient information database 152, and a patient interaction database 154 pertaining to the oral oncology medication monitoring system 100, customer profiles, web page templates and/or web pages, or other kinds of data. The server 140 may access data stored in the database 146 when executing various functions and tasks associated with the operation of the oral oncology medication monitoring system 100. As shown in FIG. 1, the program memory 160 and/or the RAM 164 may store various applications for execution by the microprocessor 162 such as an automated representative 142, a user interface 144 as discussed below. Further, the program memory 160 and/or the RAM 164 may store a server application 145 for execution by the microprocessor 162. The server application 145 operates to transmit and receive information relating to the oral oncology medication monitoring program method 200 discussed below on the network 130. The server application 145 may be a single module 238 or a plurality of modules. The server application 145 may be used in coordinating communications the various front-end components 102 and the various back-end components 104.

The back-end components 104 may include a prescriber 120, a government agency 122, and/or an insurance provider 124, which may communicate with the various front-end components 102 and the various back-end components 104 over the network 130 using a communications module 126. The prescriber 120 may be doctor, nurse, pharmacist, hospital, etc. (or a server like the server 140 associated therewith) which has prescribed an oral oncology medication to the patient. The government agency 122 may be any of a federal, state, or local agency (or a server like the server 140 associated therewith) tasked with regulatory or monitoring tasks associated with the dispensing of prescription medication (e.g., the US Food and Drug Administration, a state board of pharmacy, etc.). The insurance provider 124 may be public insurance agency or private insurance company (or a server like the server 140 associated therewith) providing prescription medication coverage for the patient. The rest of the oral oncology medication monitoring system 100 may communicate with the prescriber 120, government agency 122, and/or insurance provider 124 over the network 130 using various known methods (e.g., telephone, facsimile, digital communication over the Internet, etc.) over the network 130. The communications modules 126 may be a device (e.g., telephone, fax machine, modem, etc.) compatible to receive and interpret the method used to communicate with the prescriber 120, government agency 122, and/or insurance provider 124. Information may be gathered from and various reports may be sent to the prescriber 120, government agency 122, and/or insurance provider 124 as discussed herein.

The back-end components 104 may also include a human representative 132 and a computer terminal and/or telephone used by the human representative 132. As discussed herein, the human representative 132 may communicate with the patient over the network 130 to gather information from and distribute information to the patient in accordance with the method discussed below. The computer terminal used by the human representative 132 may include identical or similar components to the server 140. Additionally, the human representative 132 may interact with the computer terminal using any known input/output device (e.g., keyboard, mouse, microphone, touchscreen, monitor, speaker, etc.). The human representative 132 may be one of a plurality of human representatives 132 with different levels of expertise. For example, a first human representative 132 may be a lightly-trained call-center employee or contractor, a second human representative 132 may be a moderately-trained pharmacy technician, and a third human representative 132 may be a highly-trained nurse or pharmacist. The human representative 132 may manually call patients and/or use an automatic dialer.

Figure 2:
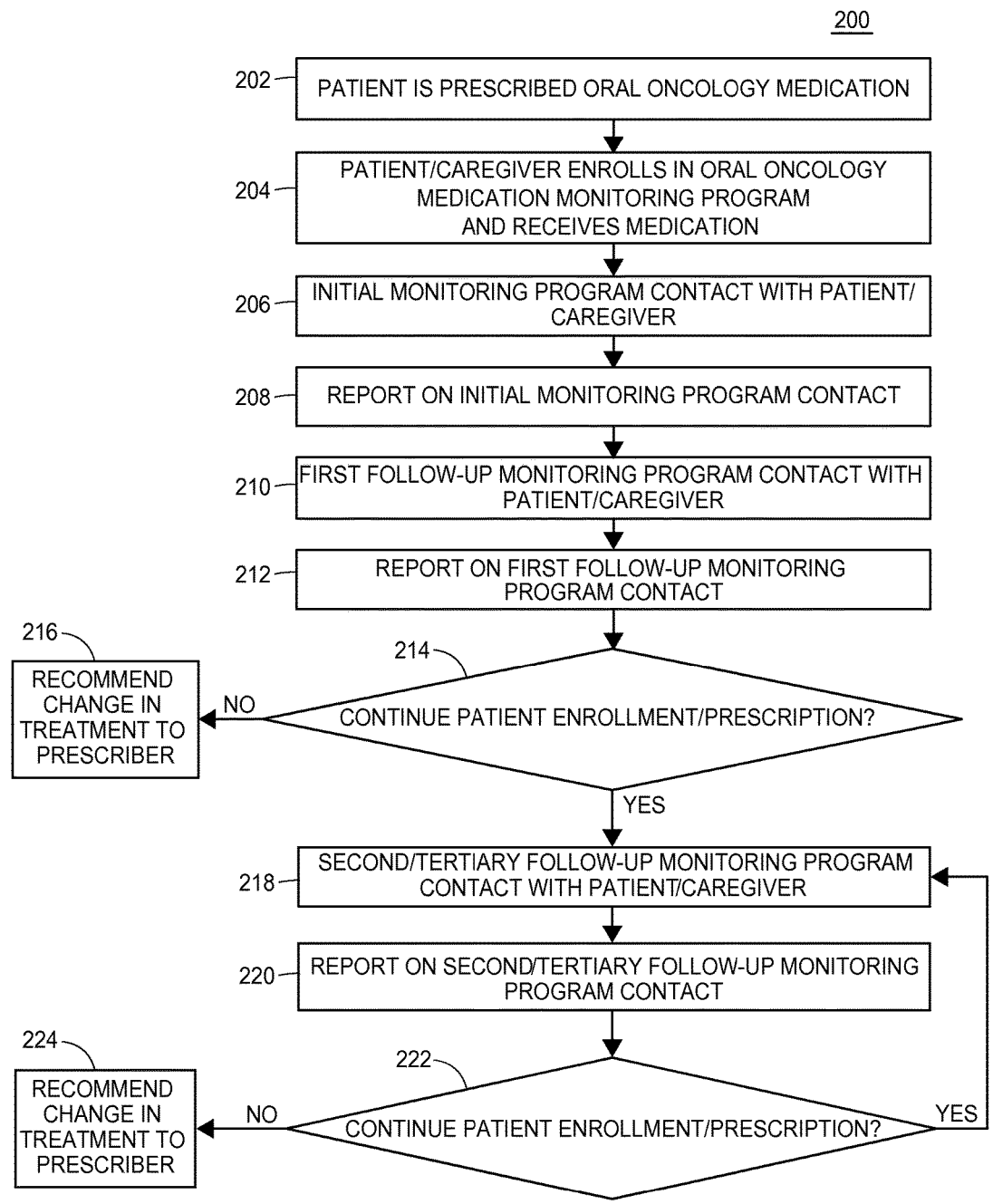
FIG. 2 depicts an exemplary oral oncology medication monitoring program method for implementing the oral oncology medication monitoring program system in accordance with the presently described embodiments.

FIG. 2 is a flow diagram depicting an exemplary embodiment of an oral oncology medication monitoring program method 200 implemented by the oral oncology medication monitoring system 100. Prior to enrollment in the oral oncology medication monitoring program, a patient is diagnosed and prescribed oral oncology medication (block 202). While the word "oral" is used in reference to the oncology medication herein, it will be understood that the outpatient oncology medication may be administered in a number of ways (e.g., oral, inhalation, injection, transdermal, etc.) The patient (or a caregiver for the patient) may then take his or her prescription to a pharmacy associated with the oral oncology medication monitoring program and enroll in the oral oncology medication monitoring program (block 204). It will be understood that the patient's prescription may be called in, faxed, or emailed to the pharmacy instead of the patient taking the prescription to the pharmacy. Additionally or alternatively, the prescriber 120 may send the prescription directly to the pharmacy. Further, the prescriber 120 may send the prescription to the pharmacy via an intermediary such as a pharmaceutical hub operating on behalf of a drug company. The patient may pickup his or her medication from a retail pharmacy or receive the medication through delivery (e.g., via the United States Postal Service®, Federal Express®, UPS®, etc.).

It may be advantageous to fill the patient's prescription as a "split fill." As used herein, a split fill refers to filling a prescription in two or more distributions. For example, if a patient is prescribed twenty-eight doses of a medication (i.e., one dose daily for twenty-eight days), split filling the prescription may include giving the patient fourteen doses initially and the remaining fourteen doses after fourteen days have passed. By split filling a prescription, the pharmacy or pharmacist may be better able to monitor how well a patient is tolerating treatment and/or how assiduously a patient is following his or her prescription or treatment plan without direct supervision by a healthcare professional (e.g., doctor, nurse, pharmacist, etc.). For example, if a patient who initially received fourteen doses comes back to the pharmacy seventeen days later for the remaining doses, then the pharmacist may easily deduce that the patient missed his or her dose at least three times. Alternatively, during a secondary or tertiary contact as discussed below, the oral oncology medication monitoring system 100 may ask the patient whether he or she has missed any doses directly. It may be preferable to split fill a patient's first set(s) of doses to determine whether the patient will assiduously follow his or her prescription sooner rather than later (e.g., after fourteen days rather than after twenty-eight days), especially for serious illnesses such as cancer. Additionally or alternatively, the split fill decision may be based on how well the patient is tolerating treatment (e.g., whether the patient's side effects are too severe to continue treatment) or whether the patient is still alive. If a patient whose prescription has been split filled is not tolerating the treatment well and/or has proven to not take his or her medication assiduously without supervision, it may be advantageous for the pharmacist to consult the prescriber to make the split fill decision and to give the prescriber the opportunity to change the treatment plan to include more supervision, a lower dosage, or different medication (discussed below in relation to block 222). For example, if a patient has shown that he misses too many doses of his daily oral oncology medication, his doctor may alter the treatment plan so that the patient comes into the doctor's office to receive weekly intravenous doses of the same medication. It may be advantageous to split fill a patient's first three sets of doses. Accordingly, a patient may be carefully monitored and receive the benefit of a split fill or refill decision, as discussed herein, every fourteen days for the first three months of treatment.

Figure 3A:
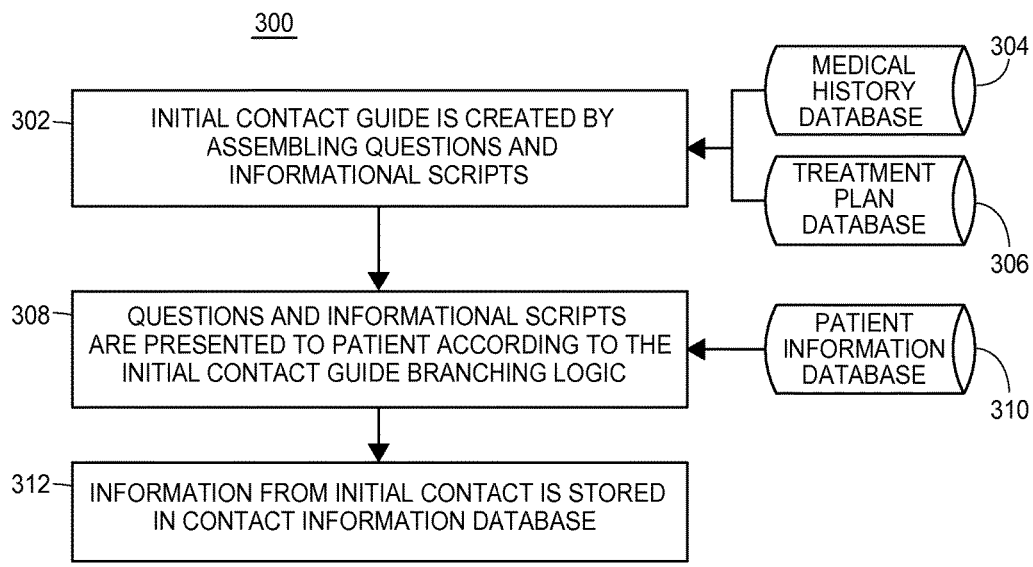
FIG. 3A depicts an exemplary initial contact method for implementing the oral oncology medication monitoring program system in accordance with the presently described embodiments.

Around the time the patient receives his or her oral oncology medication (e.g., the expected pickup or delivery date, one week before, a day after pickup, etc.), the patient may receive an initial contact from the oral oncology medication monitoring program (block 206). FIG. 3A below describes the initial contact with the patient in further detail. Once the initial contact has been conducted, the oral oncology medication monitoring system 100 may prepare one or more reports based on the initial contact (block 212). The one or more reports may include information gathered from the patient during the initial contact and/or a record of what questions and informational scripts were presented in the initial contact. The one or more reports may be generated for any number of third parties such as the prescriber 120, one or more government agencies (e.g., the Food and Drug Administration) 122, one or more insurance providers 124, etc. For example, the one or more reports may include a report to the prescriber 120 of the doses taken by the patient, side effects experienced by the patient, and counseling provided to the patient. In another example, the one or more reports may include a report to the Food and Drug Administration to report an adverse event according to government guidelines. The one or more reports may be generated for internal analysis to determine whether to keep a particular patient enrolled in the oral oncology medication monitoring program (discussed below in connection to block 214), whether experimental questions and/or informational scripts are more effective than standard questions and/or informational scripts, whether the oral oncology medication monitoring program as a whole is financially effective, etc. The one or more reports may be made anonymous to protect the identity of the patient or may identify the patient. Further, the one or more reports may include information relating to the initial contact with the patient, information relating to a plurality of initial contacts with a plurality of patients, other information about the patient or plurality of patients (e.g., information from the patient information database 152, etc.), statistical information derived from a plurality of initial contacts with a plurality of patients, or a combination of any of the foregoing.

After generating the one or more reports, the oral oncology medication monitoring system 100 may determine whether the patient should be continued to be enrolled in the oral oncology medication monitoring program (block 214). If, for example, the patient indicates that the patient's doctor has changed the patient's prescription to a medication that is not part of the oral oncology medication monitoring program, it may be advantageous to remove the patient from the program. Of course, the patient may erroneously believe that his or her prescription has been changed, so it may be advantageous to contact the prescriber 120 for verification of any changes. If the patient is removed from the oral oncology medication monitoring program, the server 140 may send a message to the prescriber 120 informing the prescriber of the un-enrollment (block 216).

Figure 3B:
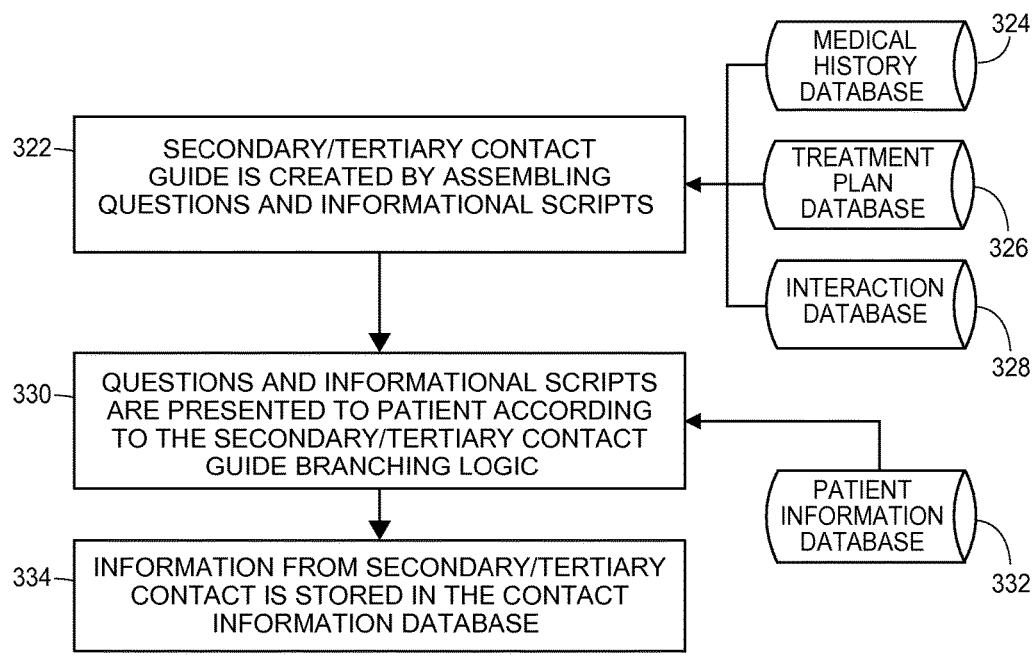
FIG. 3B depicts an exemplary secondary or tertiary contact method for implementing the oral oncology medication monitoring program system in accordance with the presently described embodiments.

After a period amount of time (i.e., a first period of time), the patient may receive a second contact from the oral oncology medication monitoring program (block 218). For example, it may be advantageous to contact the patient ten days after the initial contact or ten days after the treatment program has begun. Of course, the first period of time may be any amount of time and is not just limited to ten days. FIG. 3B below describes the secondary contact with the patient in further detail. Once the secondary contact has been conducted, the oral oncology medication monitoring system 100 may prepare one or more reports based on the secondary contact (block 220). The one or more reports may include information gathered from the patient during the secondary contact and/or a record of what questions and informational scripts were presented in the secondary contact. The one or more reports may be generated for any number of third parties such as the prescriber 120, one or more government agencies (e.g., the Food and Drug Administration) 122, one or more insurance providers 124, etc. For example, the one or more reports may include a report to the prescriber 120 of the doses taken by the patient, side effects experienced by the patient, and counseling provided to the patient. In another example, the one or more reports may include a report to the Food and Drug Administration to report an adverse event according to government guidelines. The one or more reports may be generated for internal analysis to determine whether to keep a particular patient enrolled in the oral oncology medication monitoring program (discussed below in connection to block 222), whether experimental questions and/or informational scripts are more effective than standard questions and/or informational scripts, whether the oral oncology medication monitoring program as a whole is financially effective, etc. The one or more reports may be made anonymous to protect the identity of the patient or may identify the patient. Further, the one or more reports may include information relating to the secondary contact with the patient, information relating to a plurality of secondary contacts with a plurality of patients, other information about the patient or plurality of patients (e.g., information from the patient information database 152, etc.), statistical information derived from a plurality of secondary contacts with a plurality of patients, or a combination of any of the foregoing.

After generating the one or more reports based on the secondary (or tertiary) contacts, the oral oncology medication monitoring system 100 may determine whether the patient should be continued to be enrolled in the oral oncology medication monitoring program and/or whether to refill the patient's prescription (block 222). If the patient's prescription was filled as a split fill, determining whether the patient should be continued to be enrolled in the oral oncology medication monitoring program may include determining whether to give the patient the second distribution of the split filled prescription. Determining whether the patient should be continued to be enrolled in the oral oncology medication monitoring program may include determining whether the patient missed more than a threshold number of doses during the first period of time (e.g., three doses in a fourteen day period). If the patient has missed the threshold number of doses or more, the patient may be removed from the oral oncology medication monitoring program. It may be advantageous to consult with the prescriber 120 before removing the patient from the oral oncology medication monitoring program. There may be other reasons why a patient may be removed from the oral oncology medication monitoring program, especially at the prescriber's 120 direction. For example, the patient may have been having severe side effects during the first period of time, so the patient's doctor may have changed the patient's prescription to a different medication or treatment plan or reduced the dosage of the current medication. In another example, the patient's treatment may be over because the course of treatment has been run or the patient's cancer may have gone into remission. Alternatively, the patient may die during the course of treatment. The oral oncology medication monitoring system 100 may be informed of such a change by the prescriber 120 and/or the patient. If the patient is removed from the oral oncology medication monitoring program, the server 140 may send a message to the prescriber 120 informing the prescriber of the un-enrollment (block 224).

If the patient continues enrollment in the oral oncology medication monitoring program, the patient may be given the second half of a split filled prescription or a refill of the prescription and the method 200 may loop back to block 218. After looping back and after a period of time (i.e., a second period of time), the patient may receive a tertiary contact from the oral oncology medication monitoring program (block 218). For example, it may be advantageous to contact the patient fourteen days after the secondary contact or twenty-four days after the treatment program has begun. Of course, the first period of time may be any amount of time and is not just limited to fourteen days after the secondary contact. FIG. 3B below describes the tertiary contact with the patient in further detail. Once the tertiary contact has been conducted, the oral oncology medication monitoring system 100 may prepare one or more reports based on the tertiary contact (block 220). After generating the one or more reports based on the tertiary contacts, the oral oncology medication monitoring system 100 may determine whether the patient should be continued to be enrolled in the oral oncology medication monitoring program (block 222). This determination after the second period of time may be conducted similarly to the determination made after the first period of time above, however the threshold value for missed doses may be increased (e.g., from three doses in fourteen days to seven doses over the last twenty-eight). The determination after the second period of time may additionally include determining whether the patient's treatment plan has concluded (e.g., whether the course of oral oncology therapy has been finished) and/or after consulting with the prescriber 120. If the patient continues enrollment in the oral oncology medication monitoring program, the patient may be given a refill (either a full fill or a split fill) of the prescription and the method 200 may again loop back to block 218, when the patient may receive a second tertiary contact after a third period of time. It may be advantageous for the third period to time to be fourteen days to make a second split fill determination or after the full course of the next series of doses (e.g., twenty-eight days) depending on at least information in the treatment database 150, information in the patient information database 152, and/or information in the patient interaction database 154; an instruction by the prescriber 120; or an instruction by the pharmacist dispensing the medication. In this manner, it may be advantageous to split-fill at least the first three months of a patient's oncology treatment regimen FIG. 3A is a flow diagram depicting more detail of an exemplary embodiment of the initial contact from the oral oncology medication monitoring program of block 206. As discussed above, the manner in which the patient is contacted may depend on the patient's preferences. Regardless of whether the patient is contacted by phone 110 (e.g., by a human representative 132, automated representative 142, etc.) or via a tablet computer 106, smartphone 108, and/or computer 112 (e.g., by a user interface 144), prior to contacting the patient, an initial contact guide comprising questions to ask and informational scripts to present must be created (block 302). To create the initial contact guide, the oral oncology medication monitoring system 100 may access the patient's medical history from the medical history database 148 (block 304). Additionally or alternatively, the oral oncology medication monitoring system 100 may access a treatment database 150 to gather information about the treatments in the oral oncology medication monitoring program (block 306). For example, the treatment database 150 may include standard questions and informational scripts associated with each of the oral oncology medications in the oral oncology medication monitoring program. Additionally, the treatment database 150 may include experimental questions and informational scripts associated with one or more of the oral oncology medications in the oral oncology medication monitoring program. Experimental questions and informational scripts may include rephrasing and/or rewording the standard questions and/or informational scripts such that the order, emphasis on topics, etc.

of the standard questions and informational scripts are modified. Experimental questions and informational scripts may also include additional questions and/or informational scripts. Experimental questions and informational scripts may be used to determine whether using different questions and informational scripts in initial contacts drives improved patient awareness, improved patient treatment plan compliance, improves patient satisfaction with the oral oncology medication monitoring system 100, etc.

In no particular order, the initial contact guide may contain informational scripts to provide the patient with an introduction to the oral oncology medication monitoring program and an explanation of what services are provided in association with the oral oncology medication monitoring program (e.g., follow-calls as discussed herein, split filling as discussed herein, etc.). Because many oral oncology treatments are teratogenic or may pose risks to pregnant women and developing fetuses, the initial contact guide may contain questions about a patient's likelihood of being pregnant, becoming pregnant, or being around a pregnant woman as well as informational scripts with counseling regarding the danger a medication poses to a developing fetus. The initial contact guide may include questions asking the patient for what condition they are taking the oral oncology medication to ascertain the patient's level of knowledge about his or her condition.

The initial contact guide may include questions asking the patient whether the patient has taken the oral oncology medication the patient has been prescribed in the past. The initial contact guide may include questions to determine whether the patient has begun taking the oral oncology medication, why the patient has not started taking it, and when the patient expects to begin taking the medications. The initial contact guide may also include informational scripts and questions with medication counseling to provide the patient with important information and warnings about when to take the medication, whether to take the medication with meals (e.g., take the medication in the morning with a low-fat breakfast), warnings about foods and drinks to avoid while taking the medication (e.g., do not drink grapefruit juice during Bosulif® treatment), etc. Additionally or alternatively, the initial contact guide may include questions and informational scripts regarding the health and medical history of the patient (e.g., asking whether the patient has a history of high blood pressure, informational scripts about the special risks for a patient with high blood pressure, etc.). Further, the initial contact guide may include questions and informational scripts about side effects (e.g., what types of side effects are likely, how severe side effects might be, the importance of contacting the prescriber if side effects are severe, etc.). Concluding the initial contact guide, the initial contact guide may include informational scripts to inform the patient about the secondary and tertiary contacts discussed herein.

It may be advantageous to cross reference the patient's medical history with the treatment database to determine which portions of the patient's medical history and treatment database are germane to the initial contact. For example, the patient's medical history may indicate that the patient has been prescribed Stivarga® and/or that the patient has been diagnosed with colorectal cancer (CRC) for which Stivarga® is a treatment. Accordingly, the questions and informational scripts associated with treatment plans for other medications that are not Stivarga® may be excluded from the initial contact guide. The initial contact guide may contain all of the questions and informational scripts associated with an initial contact for a particular treatment plan (e.g., Stivarga® treatment, etc.). The initial contact guide may be structured as branching logic and may contain sets of mutually exclusive questions and informational scripts as discussed in relation to FIGS. 4A, 4B, and 4C below. For example, the initial contact guide may contain one or more questions and informational scripts for women of child-bearing potential and also one or more question and informational scripts for women not of child-bearing potential.

Once the initial contact guide has been created, the initial contact guide may be used to conduct the initial contact with the patient including initiating contact with the patient (e.g., calling the patient, starting a chat session, launching a user interface, etc.), asking the patient questions, receiving answers from the patient, and presenting information using the initial contact guide (block 308). The initial contact guide may provide the human representative 132, automated representative 142, and/or user interface 144 a particular order in which to conduct the initial contact.

For example, a human representative 132 or automated representative 142 may call the patient via the patient's telephone 110 and conduct a conversation with the patient according to the initial contact guide. If the conversation is being conducted by a human representative 132, the initial contact guide may be presented to the human representative 132 as a user interface to instruct the human representative 132 how the conversation should be conducted. If the conversation is being conducted by an automated representative 142, the initial contact guide may be a series of computer instructions that are executed by the automated representative 142. The conversation may include the human representative 132 or automated representative 142 and patient engaging in an audio-only conversation or an audio and video-conversation. The human representative 132 or automated representative 142 may read an informational script explaining the reason for the call and ask whether the patient has begun taking the oral oncology medication the patient was prescribed. The initial contact guide may include branching logic that adjusts the initial contact based on the patient's response (e.g., if the patient has not begun taking the oral oncology medication, the initial contact guide may instruct the human representative 132 or automated representative 142 to ask why). The initial contact may then include questions and/or informational scripts concerning proper storage of the medication, side effects associated with the medication, warnings on interactions with the medication, etc. The initial call may be recorded and/or transcribed by the oral oncology medication monitoring system 100 (e.g., by the server 140, etc.). Additionally or alternatively, the human representative 132 or automated representative 142 may record the patient's answers to questions and/or responses to informational scripts during and/or after the initial contact. The initial contact may also include interactions not included in the initial contact guide (e.g., in response to an open-ended question such as "Do you have any questions?" the patient may ask a question not covered by the initial contact guide, etc.).

Additionally or alternatively, the initial contact may include a live chat between the human representative 132 or automated representative 142 via a tablet computer 106, smartphone 108, and/or computer 112. Such a live chat may be initiated via a website or script (e.g., JavaScript). The live chat may include a one- or two-way audio, video, and/or text between the patient and the human representative 132 or automated representative 142. For example, the live chat may include audio communication similar to the telephone call described above as well as added capabilities like video and/or text. For example, instead of merely reading an informational script to the patient, the human representative 132 or automated representative 142 may use visual aids (e.g., video of the proper way to store medication, a slide presentation about possible side effects, etc.). Alternatively, the live chat may include a text-only conversation (e.g., instant messaging, SMS messaging, etc.). The live chat may include presenting the patient with a question and asking for a response in the form of a "true" or "false" or by selecting one or more multiple choice responses. Additionally or alternatively, it may be advantageous to allow the patient to enter free text to provide more detail or in response to more open-ended questions or to supplement an "other" response to a multiple choice question.

Additionally or alternatively, the initial contact may include interaction between the patient and human representative 132, automated representative 142, and/or user interface 144 using a dedicated program installed on a tablet computer 106, smartphone 108, and/or computer 112. For example, a Walgreens® app may be installed on a patient's tablet computer 106. With the dedicated program or app, the initial contact may include multimedia presentations and information to supplement live chats or telephone conversations discussed above.

Additionally, if during the initial contact, the patient asks a question to which the human representative 132, automated representative 142, and/or user interface 144 does not have an adequate answer, the initial contact may include promising to contact the patient again to provide an answer at a later date. Such a follow-up contact may be included in a regularly scheduled secondary/tertiary contact as discussed below, or may be a separate contact meant to primarily address the patient's question.

The human representative 132, automated representative 142, and/or user interface 144 may also access a patient information database 152 to automatically answer some of the questions in the initial contact guide to expedite the initial contact (block 310). For example, the patient information database 152 may contain demographic information about the patient (e.g., sex, race/ethnicity, age, etc.). Thus, the human representative 132, automated representative 142, and/or user interface 144 may avoid asking the patient unnecessary questions and decrease the likelihood that the patient will lose interest and terminate the conversation before important information about the patient's treatment can be presented.

When the initial contact has concluded, the oral oncology medication monitoring system 100 may record some or all of the information relating to the initial contact in a patient interaction database 154 (block 312). Such information may include a full record of the initial contact such as a full audio and/or video recording of the initial contact, a transcript or transcription of the initial contact, etc. Additionally or alternatively, such information may include a record of which questions and informational scripts from the initial contact guide were presented and the patient's responses to each question and informational script. The record(s) created as a result of the initial contact may be formatted in any of a number of ways (e.g., spreadsheet, database, text, audio, video, etc.). It will be appreciated that it may be advantageous to make the record to facilitate the creation of the reports to third parties as discussed herein. If the initial contact included experimental questions and/or informational scripts as discussed above, a notation may be made in the record of the initial contact for later analysis. Of course, the oral oncology medication monitoring system 100 may record the information relating to the initial contact during the initial contact as well as or as an alternative to recording the information after the contact has concluded.

FIG. 3B is a flow diagram depicting more detail of an exemplary embodiment of the secondary or tertiary contact from the oral oncology medication monitoring program of block 218. As discussed above, the manner in which the patient is contacted may depend on the patient's preferences. Regardless of whether the patient is contacted by via phone 110 (e.g., by a human representative 132, automated representative 142, etc.) or via a tablet computer 106, smartphone 108, and/or computer 112 (e.g., by a user interface 144), prior to contacting the patient, a secondary or tertiary contact guide comprising questions to ask and informational scripts to present must be created (block 322). To create the secondary or tertiary contact guide, the oral oncology medication monitoring system 100 may access the patient's medical history from the medical history database 148 (block 324). Additionally or alternatively, the oral oncology medication monitoring system 100 may access a treatment database 150 to gather information about the treatments in the oral oncology medication monitoring program (block 326). For example, the treatment database 150 may include standard questions and informational scripts associated with each of the oral oncology medications in the oral oncology medication monitoring program. Additionally, the treatment database 150 may include experimental questions and informational scripts associated with one or more of the oral oncology medications in the oral oncology medication monitoring program. Experimental questions and informational scripts may include rephrasing and/or rewording the standard questions and/or informational scripts such that the order, emphasis on topics, etc. of the standard questions and informational scripts are modified. Experimental questions and informational scripts may also include additional questions and/or informational scripts. Experimental questions and informational scripts may be used to determine whether using different questions and informational scripts in secondary or tertiary contacts drives improved patient awareness, improved patient treatment plan compliance, improves patient satisfaction with the oral oncology medication monitoring system 100, etc. Additionally or alternatively, the oral oncology medication monitoring system 100 may access the patient interaction database 154 to gather information about the answers the patient has given to previous answers (block 328). For example, the patient interaction database 154 may contain information about whether a female patient is pregnant, that a male patient lives with a woman who is pregnant, etc.

In no particular order, the secondary or tertiary contact guide may contain informational scripts to follow up with the patient participating in the oral oncology medication monitoring program to determine how the course of treatment has been going since the last contact. The secondary or tertiary contact guide may include instructions to ask the patient whether he or she is still taking the oral oncology medication, and follow up questions to ask the patient why he or she has stopped taking the medication. Further, the secondary or tertiary contact guide may include questions and informational scripts about the side effects associated with taking a particular oral oncology medication (e.g., what types of side effects are likely, how severe side effects might be, the importance of contacting the prescriber if side effects are severe, etc.). If the patient's dosage was decreased because of an adverse side-effect, the secondary or tertiary contact guide may include an informational script instructing the human representative 132, automated representative 142, etc. to tell the prescriber 120 to consider escalating the dosages back to the recommended dosage if the adverse side effect is resolved. The secondary or tertiary contact guide may include informational scripts and/or questions relating to missing doses. The secondary or tertiary contact guide may contain questions directly asking the patient whether he or she has missed a dose and follow up questions asking the patient the reason for the missed dose. The secondary or tertiary contact guide may also include reminders of the medication counseling provided in the initial contact (e.g., warnings for teratogenic medication, instruction on when and how to take medication, etc.). Concluding the secondary or tertiary contact guide, the secondary or tertiary contact guide may include informational scripts to remind the patient to refill his or her prescription and inform the patient about further tertiary contacts.

It may be advantageous to cross reference the patient's medical history 148 with the treatment database 150 and patient interaction database 154 to determine which portions of the patient's medical history and treatment database are germane to the secondary or tertiary contact. For example, the patient's medical history may indicate that the patient has been prescribed Stivarga® and/or that the patient has been diagnosed with colorectal cancer (CRC) for which Stivarga® is a treatment. Accordingly, the questions and informational scripts associated with treatment plans for other medications that are not Stivarga® may be excluded from the secondary or tertiary contact guide. The secondary or tertiary contact guide may contain all of the questions and informational scripts associated with a secondary or tertiary contact for a particular treatment plan (e.g., Stivarga® treatment, etc.). The secondary or tertiary contact guide may be structured as branching logic and may contain sets of mutually exclusive questions and informational scripts as discussed in relation to FIGS. 4A, 4B, and 4C below. For example, the secondary or tertiary contact guide may contain one or more questions and informational scripts for women of child-bearing potential and also one or more question and informational scripts for women not of child-bearing potential.

Once the secondary or tertiary contact guide has been created, the secondary or tertiary contact guide may be used to conduct the secondary or tertiary contact with the patient including initiating contact with the patient (e.g., calling the patient, starting a chat session, launching a user interface, etc.), asking the patient questions, receiving answers from the patient, and presenting information using the secondary or tertiary contact guide (block 330). The secondary or tertiary contact guide may provide the human representative 132, automated representative 142, and/or user interface 144 a particular order in which to conduct the secondary or tertiary contact.

For example, a human representative 132 or automated representative 142 may call the patient via the patient's telephone 110 and conduct a conversation with the patient according to the secondary or tertiary contact guide. If the conversation is being conducted by a human representative 132, the secondary or tertiary contact guide may be presented to the human representative 132 as a user interface to instruct the human representative 132 how the conversation should be conducted. If the conversation is being conducted by an automated representative 142, the secondary or tertiary contact guide may be a series of computer instructions that are executed by the automated representative 142. The conversation may include the human representative 132 or automated representative 142 and patient engaging in an audio-only conversation or an audio and video-conversation. The human representative 132 or automated representative 142 may read an informational script explaining the reason for the call and ask whether the patient has begun taking the oral oncology medication the patient was prescribed. The secondary or tertiary contact guide may include branching logic that adjusts the secondary or tertiary contact based on the patient's response (e.g., if the patient has missed three or more doses of the oral oncology medication, the secondary or tertiary contact guide may instruct the human representative 132 or automated representative 142 to ask why). The secondary or tertiary contact may then include questions and/or informational scripts concerning proper storage of the medication, side effects associated with the medication, warnings on interactions with the medication, etc. The secondary or tertiary call may be recorded and/or transcribed by the oral oncology medication monitoring system 100 (e.g., by the server 140, etc.). Additionally or alternatively, the human representative 132 or automated representative 142 may record the patient's answers to questions and/or responses to informational scripts during and/or after the secondary or tertiary contact. The secondary or tertiary contact may also include interactions not included in the secondary or tertiary contact guide (e.g., in response to an open-ended question such as "Do you have any questions?" the patient may ask a question not covered by the secondary or tertiary contact guide, etc.).

Additionally or alternatively, the secondary or tertiary contact may include a live chat between the human representative 132 or automated representative 142 via a tablet computer 106, smartphone 108, and/or computer 112. Such a live chat may be initiated via a website or script (e.g., JavaScript). The live chat may include a one- or two-way audio, video, and/or text between the patient and the human representative 132 or automated representative 142. For example, the live chat may include audio communication similar to the telephone call described above as well as added capabilities like video and/or text. For example, instead of merely reading an informational script to the patient, the human representative 132 or automated representative 142 may use visual aids (e.g., video of the proper way to store medication, a slide presentation about possible side effects, etc.). Alternatively, the live chat may include a text-only conversation (e.g., instant messaging, SMS messaging, etc.). The live chat may include presenting the patient with a question and asking for a response in the form of a "true" or "false" or by selecting one or more multiple choice responses. Additionally or alternatively, it may be advantageous to allow the patient to enter free text to provide more detail or in response to more open-ended questions or to supplement an "other" response to a multiple choice question.

Additionally or alternatively, the secondary or tertiary contact may include interaction between the patient and human representative 132, automated representative 142, and/or user interface 144 using a dedicated program installed on a tablet computer 106, smartphone 108, and/or computer 112. For example, a Walgreens® app may be installed on a patient's tablet computer 106. With the dedicated program or app, the secondary or tertiary contact may include multimedia presentations and information to supplement live chats or telephone conversations discussed above.

Additionally, if during the secondary or tertiary contact, the patient asks a question to which the human representative 132, automated representative 142, and/or user interface 144 does not have an adequate answer, the secondary or tertiary contact may include promising to contact the patient again to provide an answer at a later date. Such a follow-up contact may be included in a regularly scheduled tertiary contact, or may be a separate contact meant to primarily address the patient's question.

The human representative 132, automated representative 142, and/or user interface 144 may also access a patient information database 152 to automatically answer some of the questions in the secondary or tertiary contact guide to expedite the secondary or tertiary contact (block 310). For example, the patient information database 152 may contain demographic information about the patient (e.g., sex, race/ethnicity, age, etc.). Thus, the human representative 132, automated representative 142, and/or user interface 144 may avoid asking the patient unnecessary questions and decrease the likelihood that the patient will lose interest and terminate the conversation before important information about the patient's treatment can be presented.

When the secondary or tertiary contact has concluded, the oral oncology medication monitoring system 100 may record some or all of information relating to the secondary or tertiary contact in a patient interaction database 154 (block 334). Such information may include a full record of the secondary or tertiary contact such as a full audio and/or video recording of the secondary or tertiary contact, a transcript or transcription of the secondary or tertiary contact, etc. Additionally or alternatively, such information may include a record of which questions and informational scripts from the secondary or tertiary contact guide were presented and the patient's responses to each question and informational script. The record(s) created as a result of the secondary or tertiary contact may be formatted in any of a number of ways (e.g., spreadsheet, database, text, audio, video, etc.). It will be appreciated that it may be advantageous to make the record to facilitate the creation of the reports to third parties as discussed herein. If the secondary or tertiary contact included experimental questions and/or informational scripts as discussed above, a notation may be made in the record of the secondary or tertiary contact for later analysis. Of course, the oral oncology medication monitoring system 100 may record the information relating to the secondary or tertiary contact during the secondary or tertiary contact as well as or as an alternative to recording the information after the contact has concluded.

Figure 4C:
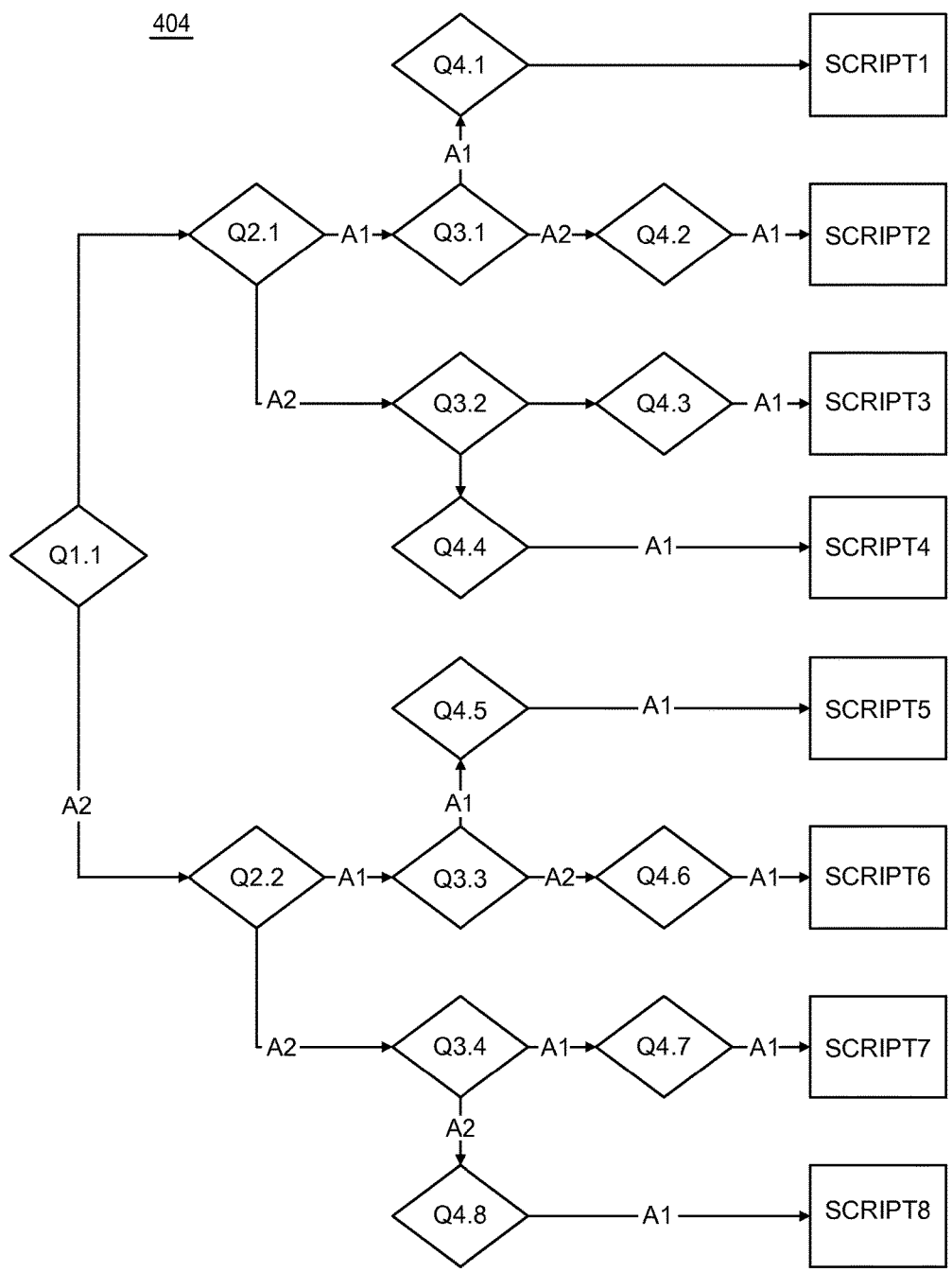

FIGS. 4A, 4B, and 4C are examples of branching logic employed in the initial contact guide and the secondary/tertiary contact guide discussed below. FIG. 4A depicts a linear branching logic 402. The linear branching logic 402 may be used for contact guides comprising questions and scripts that are asked in series but further comprise questions where certain answers may cause portions of the contact guide to be skipped. For example, if a medication in the oral oncology monitoring program is known to be teratogenic, the contact guide may include questions and informational scripts directed to women of child-bearing potential. Accordingly, if the patient responds in the negative to the question "Are you a woman of child-bearing potential?" a contact guide with linear branching logic may skip the questions and informational scripts directed to women of child-bearing potential." As shown in FIG. 4A, if a patient responds to Q1 with the answer A1, the linear branching logic 402 advances to SCRIPT1. However, if a patient responds to Q1 with the answer A2, the linear branching logic 402 may skip SCRIPT1 and Q2 and advance directly to SCRIPT2.

FIG. 4C depicts a mutually exclusive branching logic 406. The mutually exclusive branching logic 406 comprises a number of informational scripts (i.e., SCRIPT1-8) of which one informational script is presented after the patient answers a series of questions. For example, if the patient answers A1 to Q1.1, A1 to Q2.1, A2 to Q3.1, and A1 to Q4.2, SCRIPT2 will be presented to the patient. Similarly, if the patient answers A2 to Q1.1, A2 to Q2.2, A2 to Q3.4, and A1 to Q4.8, SCRIPT8 will be presented to the patient. For example, Q1.1 might be "Are you male or female?" where A1 corresponds to "male" and A2 corresponds to "female." Having answered "female" to Q1.1, Q2.2 might be "Do you smoke?" where A1 corresponds to "yes" and A2 corresponds to "no." In this way, the informational script presented at the end of the mutually exclusive branching logic 406 can be tailored to the patient's individual characteristics.

FIG. 4B depicts a hybrid branching logic 404 with both linear and mutually exclusive branching logic. For example, the hybrid branching logic 404 includes mutually exclusive questions Q2.1 and Q2.2 based on the patient's response to question Q1.1. However, regardless of the answers to Q1.1, the SCRIPT4 will be presented to the patient at the end of the hybrid branching logic.

Of course, it will be understood that the initial contact guide and/or the secondary/tertiary contact guide may include elements of any, some, or all of the branching logic examples 402, 404, and 406. For example, an initial contact guide may begin with linear branching logic and end with mutually exclusive branching logic, or vice versa. Additionally, it will be understood that while the examples presented above include questions with only two answers, questions may have any number of answers. For example, a question may be "To which race or ethnic group do you belong?" to which there might be tens of answers.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed:

1. A method for communicating with a patient on an outpatient oral oncology regimen, the method executed by one or more processors programmed to perform the method, the method comprising:

creating, by one or more processors, an initial contact guide to direct a patient interaction occurring at the beginning of the outpatient oral oncology regimen, wherein the initial contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented, wherein the one or more questions are selected from a plurality of questions which are filtered based at least in part on teratogenicity of the outpatient oral oncology regimen and at least some of the filtered plurality of questions are automatically answered, by the one or more processors, based on medical history data and treatment data for the patient from a medical history database and a treatment database, respectively, and wherein the one or more questions include at least one experimental question in a different format than an original format for a corresponding question to determine whether the different format improves patient compliance;

using, by the one or more processors, the initial contact guide to conduct an initial contact with the patient by:
 (i) presenting a first initial contact question to the patient,
 (ii) receiving an initial contact answer from the patient wherein the initial contact answer is stored in a patient interaction database,
 (iii) using the branching logic of the initial contact guide to determine which initial contact guide questions and informational scripts to present based on the initial contact answer, and
 (iv) presenting one or more subsequent questions or informational scripts based on the determination of which initial contact guide questions and informational scripts to present based on the initial contact answer, wherein the initial contact with the patient is conducted by an automated representative;

creating, by the one or more processors, a secondary contact guide to direct a patient interaction occurring a first period of time after the beginning of the outpatient oral oncology regimen, wherein the secondary contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented;

using, by the one or more processors, the secondary contact guide to conduct a secondary contact with the patient by:
 (i) after the first period of time after the beginning of the outpatient oral oncology regimen, presenting a first secondary contact question to the patient,
 (ii) receiving a secondary contact answer from the patient wherein the secondary contact answer is stored in a patient interaction database,
 (iii) using the branching logic of the secondary contact guide to determine which secondary contact guide questions and informational scripts to present based on the secondary contact answer, and
 (iv) presenting one or more subsequent questions or informational scripts based on the determination of which secondary contact guide questions and informational scripts to present based on the secondary contact answer, wherein the secondary contact with the patient is conducted by the automated representative;

preparing, by the one or more processors, a report based on one or more of the initial contact or secondary contact; and sending, by the one or more processors, the report to a third party including one or more of a prescriber of the outpatient oral oncology regimen, a government agency, or an insurance provider, wherein the report includes indications of one or more adverse effects caused by the outpatient oral oncology regimen.

2. The method of claim 1, further comprising, dispensing a prescription for an oncologic medication.

3. The method of claim 2, wherein dispensing the prescription for an oncologic medication includes split-filling the prescription for the oncologic medication, wherein a first portion of the prescription is dispensed at substantially the beginning of the outpatient oral oncology regimen, the method further comprising:
 determining whether to dispense a second portion of the prescription based on one or more of whether the patient has missed more than a threshold number of doses of the oncologic medication, how well the patient has tolerated the outpatient oral oncology regimen, a consultation with the prescriber of the outpatient oral oncology regimen, or whether the patient is still alive;
 based on the determination of whether to dispense the second portion of the prescription, dispensing or not dispensing the second portion of the prescription.

4. The method of claim 1, wherein the initial contact and secondary contact are conducted using one or more of a telephone, computer, tablet computer, or mobile phone.

5. The method of claim 1, wherein prior to presenting the first initial contact question to the patient, receiving information about the patient from the patient information database.

6. The method of claim 1, wherein prior to presenting the first secondary contact question to the patient, receiving information about the patient from the patient information database.

7. The method of claim 1, wherein the one or more questions and one or more informational scripts of the initial contact guide and secondary contact guide relate to one or more of the side effects associated with the outpatient oral oncology regimen, medication counseling associated with the outpatient oral oncology regimen, missed doses in the outpatient oral oncology regimen, or ascertain the patient's level of knowledge about the outpatient oral oncology regimen.

8. A computer system for communicating with a patient on an outpatient oral oncology regimen, comprising:
 a processor;
 a memory storing computer executable instructions that when executed by the processor cause the computer system to:
  create an initial contact guide to direct a patient interaction occurring at the beginning of the outpatient oral oncology regimen, wherein the initial contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented, wherein the one or more questions are selected from a plurality of questions which are filtered based at least in part on teratogenicity of the outpatient oral oncology regimen and at least some of the filtered plurality of questions are automatically answered based on medical history data and treatment data for the patient from a medical history database and a treatment database, respectively, and wherein the one or more questions include at least one experimental question in a different format than an original format for a corresponding question to determine whether the different format improves patient compliance;

use the initial contact guide to conduct an initial contact with the patient by:
  (i) present a first initial contact question to the patient,
  (ii) receive an initial contact answer from the patient wherein the initial contact answer is stored in a patient interaction database,
  (iii) use the branching logic of the initial contact guide to determine which initial contact guide questions and informational scripts to present based on the initial contact answer, and
  (iv) present one or more subsequent questions or informational scripts based on the determination of which initial contact guide questions and informational scripts to present based on the initial contact answer, wherein the initial contact with the patient is conducted by an automated representative;

create a secondary contact guide to direct a patient interaction occurring a first period of time after the beginning of the outpatient oral oncology regimen, wherein the secondary contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented;

use the secondary contact guide to conduct a secondary contact with the patient by:
  (i) after the first period of time after the beginning of the outpatient oral oncology regimen, present a first secondary contact question to the patient,
  (ii) receive a secondary contact answer from the patient wherein the secondary contact answer is stored in a patient interaction database,
  (iii) use the branching logic of the secondary contact guide to determine which secondary contact guide questions and informational scripts to present based on the secondary contact answer, and
  (iv) present one or more subsequent questions or informational scripts based on the determination of which secondary contact guide questions and informational scripts to present based on the secondary contact answer, wherein the secondary contact with the patient is conducted by the automated representative;

prepare a report based on one or more of the initial contact or secondary contact; and send the report to a third party including one or more of a prescriber of the outpatient oral oncology regimen, a government agency, or an insurance provider, wherein the report includes indications of one or more adverse effects caused by the outpatient oral oncology regimen.

9. The computer system of claim 8, wherein the memory stores further instructions that when executed by the processor cause the computer system to facilitate dispensing a prescription for an oncologic medication.

10. The computer system of claim 8, wherein the memory stores further instructions that when executed by the processor cause the computer system to:
  facilitate split-filling the prescription for the oncologic medication, wherein a first portion of the prescription is dispensed at substantially the beginning of the outpatient oral oncology regimen;
  determine whether to dispense a second portion of the prescription based on one or more of whether the patient has missed more than a threshold number of doses of the oncologic medication, how well the patient has tolerated the outpatient oral oncology regimen, a consultation with the prescriber of the outpatient oral oncology regimen, or whether the patient is still alive;
  based on the determination of whether to dispense the second portion of the prescription, facilitate dispensing or not facilitate dispensing the second portion of the prescription.

11. The computer system of claim 8, wherein the initial contact and secondary contact are conducted using one or more of a telephone, computer, tablet computer, or mobile phone.

12. The computer system of claim 8, wherein the memory stores further instructions that when executed by the processor cause the computer system to receive information about the patient from a patient information database prior to presenting the first initial contact question to the patient.

13. The computer system of claim 8, wherein the memory stores further instructions that when executed by the processor cause the computer system to receive information about the patient from a patient information database prior to presenting the first secondary contact question to the patient.

14. The computer system of claim 8, wherein the one or more questions and one or more informational scripts of the initial contact guide and secondary contact guide relate to one or more of the side effects associated with the outpatient oral oncology regimen, medication counseling associated with the outpatient oral oncology regimen, missed doses in the outpatient oral oncology regimen, or ascertain the patient's level of knowledge about the outpatient oral oncology regimen.

15. A tangible, computer-readable medium storing instructions that when executed by a processor cause a computer system to:
  create an initial contact guide to direct a patient interaction occurring at the beginning of the outpatient oral oncology regimen, wherein the initial contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented, wherein the one or more questions are selected from a plurality of questions which are filtered based at least in part on teratogenicity of the outpatient oral oncology regimen and at least some of the filtered plurality of questions are automatically answered based on medical history data and treatment data for the patient from a medical history database and a treatment database, respectively, and wherein the one or more questions include at least one experimental question in a different format than an original format for a corresponding question to determine whether the different format improves patient compliance;

use the initial contact guide to conduct an initial contact with the patient by:
(i) present a first initial contact question to the patient,
(ii) receive an initial contact answer from the patient wherein the initial contact answer is stored in a patient interaction database,
(iii) use the branching logic of the initial contact guide to determine which initial contact guide questions and informational scripts to present based on the initial contact answer, and
(iv) present one or more subsequent questions or informational scripts based on the determination of which initial contact guide questions and informational scripts to present based on the initial contact answer, wherein the initial contact with the patient is conducted by an automated representative;

create a secondary contact guide to direct a patient interaction occurring a first period of time after the beginning of the outpatient oral oncology regimen, wherein the secondary contact guide includes one or more questions about the outpatient oral oncology regimen, one or more informational scripts providing information to the patient regarding the outpatient oral oncology regimen, and branching logic to determine which questions and informational scripts to present and an order in which questions and informational scripts are presented;

use the secondary contact guide to conduct a secondary contact with the patient by:
(i) after the first period of time after the beginning of the outpatient oral oncology regimen, present a first secondary contact question to the patient,
(ii) receive a secondary contact answer from the patient wherein the secondary contact answer is stored in a patient interaction database,
(iii) use the branching logic of the secondary contact guide to determine which secondary contact guide questions and informational scripts to present based on the secondary contact answer, and
(iv) present one or more subsequent questions or informational scripts based on the determination of which secondary contact guide questions and informational scripts to present based on the secondary contact answer, wherein the secondary contact with the patient is conducted by the automated representative;

prepare a report based on one or more of the initial contact or secondary contact; and send the report to a third party including one or more of a prescriber of the outpatient oral oncology regimen, a government agency, or an insurance provider, wherein the report includes indications of one or more adverse effects caused by the outpatient oral oncology regimen.

16. The tangible, computer-readable medium of claim 15, further storing instructions that when executed by the processor cause the computer system to facilitate dispensing a prescription for an oncologic medication.

17. The tangible, computer-readable medium of claim 15, further storing instructions that that when executed by the processor cause the computer system to:
facilitate split-filling the prescription for the oncologic medication, wherein a first portion of the prescription is dispensed at substantially the beginning of the outpatient oral oncology regimen;
determine whether to dispense a second portion of the prescription based on one or more of whether the patient has missed more than a threshold number of doses of the oncologic medication, how well the patient has tolerated the outpatient oral oncology regimen, a consultation with the prescriber of the outpatient oral oncology regimen, or whether the patient is still alive;
based on the determination of whether to dispense the second portion of the prescription, facilitate dispensing or not facilitate dispensing the second portion of the prescription.

18. The tangible, computer-readable medium of claim 15, wherein the initial contact and secondary contact are conducted using one or more of a telephone, computer, tablet computer, or mobile phone.

19. The tangible, computer-readable medium of claim 15, further storing instructions that that when executed by the processor cause the computer system to receive information about the patient from a patient information database prior to presenting the first initial contact question to the patient.

20. The tangible, computer-readable medium of claim 15, further storing instructions that that when executed by the processor cause the computer system to receive information about the patient from a patient information database prior to presenting the first initial contact question to the patient.

21. The tangible, computer-readable medium of claim 15, wherein the one or more questions and one or more informational scripts of the initial contact guide and secondary contact guide relate to one or more of the side effects associated with the outpatient oral oncology regimen, medication counseling associated with the outpatient oral oncology regimen, missed doses in the outpatient oral oncology regimen, or ascertain the patient's level of knowledge about the outpatient oral oncology regimen.

* * * * *